United States Patent
Link

(10) Patent No.: US 11,419,728 B2
(45) Date of Patent: Aug. 23, 2022

(54) IMPLANT FOR RECONSTRUCTING AN ACETABULUM AND AT LEAST PART OF A PELVIC STRUCTURE

(71) Applicant: Waldemar Link GmbH & Co. KG, Hamburg (DE)

(72) Inventor: Helmut D Link, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 0 days.

(21) Appl. No.: 16/073,909

(22) PCT Filed: Jan. 30, 2017

(86) PCT No.: PCT/EP2017/051901
§ 371 (c)(1),
(2) Date: Jul. 30, 2018

(87) PCT Pub. No.: WO2017/140478
PCT Pub. Date: Aug. 24, 2017

(65) Prior Publication Data
US 2019/0038420 A1 Feb. 7, 2019

(30) Foreign Application Priority Data
Feb. 16, 2016 (DE) .................... 10 2016 202 333.0

(51) Int. Cl.
| A61F 2/34 | (2006.01) |
| A61F 2/28 | (2006.01) |
| A61F 2/30 | (2006.01) |

(52) U.S. Cl.
CPC .................. *A61F 2/34* (2013.01); *A61F 2/28* (2013.01); *A61F 2/30942* (2013.01);
(Continued)

(58) Field of Classification Search
CPC .............. A61F 2/34; A61F 2002/30995; A61F 2002/30245; A61F 2002/30324; A61F 2002/30593
See application file for complete search history.

(56) References Cited

U.S. PATENT DOCUMENTS

| 5,326,367 A | 7/1994 | Robioneck |
| 7,670,383 B1 | 3/2010 | Brown et al. |

(Continued)

FOREIGN PATENT DOCUMENTS

| CN | 102048598 A | 5/2011 |
| CN | 102614035 A | 1/2012 |

(Continued)

OTHER PUBLICATIONS

"Integral," Dictionary.com; Apr. 1, 2016. Retrieved from: https://web.archive.org/web/20160401154125/https://www.dictionary.com/browse/integral (Year: 2016).*

(Continued)

*Primary Examiner* — Yashita Sharma
*Assistant Examiner* — Amanda M Barkan
(74) *Attorney, Agent, or Firm* — Chiesa Shahinian & Giantomasi

(57) ABSTRACT

The present invention provides an implant for reconstructing an acetabulum and at least part of a pelvic structure. To this end, the implant comprises a frame structure embodied by at least one first profile element for transferring joint forces, a joint section which forms at least part of an artificial acetabulum, at least two attachment sections for attaching the implant to bone tissue, wherein a first attachment section is provided for attachment to a sacral bone or iliac bone and a second attachment section is provided for attachment to a (Continued)

pubic bone, and at least one plate element for supporting internal organs, which is surrounded by the frame structure, at least in sections.

12 Claims, 2 Drawing Sheets

(52) U.S. Cl.
CPC .. *A61F 2/30988* (2013.01); *A61F 2002/3097* (2013.01); *A61F 2002/30245* (2013.01); *A61F 2002/30433* (2013.01); *A61F 2002/30985* (2013.01); *A61F 2002/30995* (2013.01)

(56) References Cited

U.S. PATENT DOCUMENTS

| | | | | |
|---|---|---|---|---|
| 8,361,126 | B2* | 1/2013 | Perrow | A61B 17/8891 606/287 |
| 8,597,365 | B2* | 12/2013 | Meridew | A61F 2/34 623/22.32 |
| 9,700,418 | B2* | 7/2017 | Melozzi | A61F 2/32 |
| 9,808,261 | B2* | 11/2017 | Gelaude | A61B 17/1746 |
| 10,433,965 | B2* | 10/2019 | de Beaubien | A61F 2/38 |
| 2006/0166775 | A1 | 7/2006 | Gradu | |

FOREIGN PATENT DOCUMENTS

| | | |
|---|---|---|
| CN | 202654269 U | 1/2013 |
| CN | 202665752 U | 1/2013 |
| CN | 103040546 A | 4/2013 |
| DE | 3027063 A1 | 2/1982 |
| DE | 4133433 C1 | 5/1993 |
| EP | 2764848 A1 | 8/2014 |
| JP | H0523363 A | 2/1993 |
| JP | H0231750 A | 1/2005 |
| WO | 88/01491 A1 | 3/1988 |

OTHER PUBLICATIONS

China National Intellectual Property Administration, First Notification of Office Action, App. No. 201780011140.0, dated Aug. 13, 2019 (6 pages).
PCT International Search Report for application WO 2017/140478, dated Apr. 13, 2017 (13 pages).
Search Report for application DE 10 2016 202 330.0, dated Oct. 24, 2016 (86 pages).

* cited by examiner

IMPLANT FOR RECONSTRUCTING AN ACETABULUM AND AT LEAST PART OF A PELVIC STRUCTURE

CROSS REFERENCE TO RELATED APPLICATIONS

This application is a National Stage of International Application No. PCT/EP2017/051901 filed on Jan. 30, 2017, claiming priority based on German Patent Application No. DE 10 2016 202 333.0 filed on Feb. 16, 2016. The contents of each of the above documents is incorporated herein by reference in their entirety.

FIELD OF THE INVENTION

The present invention relates to an implant for reconstructing or replacing an acetabulum and at least part of a pelvic structure.

BACKGROUND

The established standard artificial hip-joint implants that are used are inadequate for treating patients who have experienced severe damage or even loss of part of their pelvic structure. Due to the loss of bone tissue in such cases, it is difficult or even impossible to adequately anchor endoprostheses of this kind. Such a situation can arise following repair or even re-repair of a hip endoprosthesis due to wear or inflammation. Other reasons for loss of part of the pelvic structure are accidents or cancers. All in all, this situation requires a patient-specific solution that is capable of replacing the lost or damaged bone tissue.

Here the aim is to replace or reconstruct the damaged or missing part of the pelvic structure, so that the pelvis once again has an articular socket for an artificial hip joint. This is a precondition for restoring the patient's mobility and hence their quality of life.

An approach known from the prior art as a "Tri-Flange Cup Implant" is to reconstruct the missing part of the pelvic structure in anatomically accurate manner or, if this is not possible due to the lack of sufficient information, to approximate it as accurately as possible from the mirror-image counterpart of the pelvic structure.

However, such complex replication of the pelvic structure does not have any apparent medical advantage. A metal implant made in this way is an order of magnitude heavier and more rigid than the native original. Replacement of the ilium, in particular, involves replacing quite a considerable volume of bone with the metal of the prosthesis. Consequently, the resulting implant is not only heavy but considerably overdimensioned in terms of strength, since the main purpose of an ilium replacement is to support the patient's internal organs, thereby preventing hernias, for example.

Particularly where a larger section of a pelvic structure is being replaced, for example a complete side of a pelvis including ilium, ischium and pubis, the weight of a replacement known from the prior art can lead to problems in bonding to the existing bone tissue. Particularly straight after the operation, there is a danger of overloading at the connection points for the implant and, in the worst case, of further damage to the patient's tissue.

Moreover, reconstruction of the bone geometry involves a complex fabrication, which, although patient-specific, is also a costly option for replacing the pelvic structure and the hip joint.

SUMMARY OF THE INVENTION

The object of the present invention was therefore to provide an implant that primarily replaces the acetabulum and at least part of the pelvic structure. The aim was for the implant to allow a suitable attachment to existing bone tissue and, despite the replacement of missing or damaged bone structures, to be lighter than known solutions. The implant was also intended to provide stable support and protection for surrounding organs. A further aim was to minimise the manufacturing costs and construction costs of a customised implant, despite the high patient-specific requirements.

In order to meet these challenges, the present invention provides an implant for reconstructing an acetabulum and at least part of a pelvic structure. To this end, the implant comprises a frame structure embodied by at least one first profile element for transferring joint forces, a joint section, which forms at least part of an artificial acetabulum, at least two attachment sections for attaching the implant to bone tissue, wherein a first attachment section is provided for attachment to a sacral bone or iliac bone and a second attachment is provided for attachment to a pubic bone, and at least one plate element for supporting internal organs, which is surrounded by the frame structure, at least in sections.

With the aid of the frame structure and the at least one plate element, the structural tasks of the implant are substantially shared. The frame structure primarily assumes the transfer of joint forces between the joint section and the bone tissue or the patient's skeleton. In contrast, the at least one plate element primarily serves to support internal organs in the form of a supporting and separating wall stretched between the frame structure and preferably spatially curved.

This combination allows the weight of the implant to be considerably reduced. Also, an implant constructed in this way is not as rigid as the above-mentioned tri-flange implants known from the prior art. Consequently, the rigidity of the implant is closer to that of the bone tissue it is replacing, which allows more physiological induction of forces via the implant into the adjoining or attached bone tissue.

Due to the fact that the plate element is surrounded by the frame structure, at least in sections, the at least one profile element forming the frame structure prevents internal organs from being damaged by the circumferential edge of the plate element. Consequently, the combination of plate element and frame structure provides reliable support and, at the same time, tissue-friendly contact with the internal organs, thereby preventing the occurrence of hernias, for example.

Thus the implant makes better use of the material properties than anatomically modelled implants. This results in a functionally-oriented design, both in terms of strength and also manufacture of the implant. In particular, a specific deformation or a specific elastic behaviour can be achieved by changing the cross-section and material thickness of the profile.

Depending upon the extent of the loss of or damage to bone tissue, the implant according to the invention is not only able to replace the hip socket (acetabulum) but also part of the pubis (os pubis) and part or all of the ilium (os ilium).

The attachment sections allow attachment of the implant to the bones, wherein said attachment can be provided as a fixed connection and/or a support.

In a further particularly preferred embodiment, the implant has a second frame structure embodied by at least one profile element to replace at least a part of an ischium.

With this preferred embodiment it is possible to retain the supporting function of the ischium, thereby also helping to maintain the patient's quality of life.

According to a further embodiment, the second frame structure further comprises a plate element and/or an attachment section.

Also in the case of the ischium, the plate element fulfils a supporting function and, in combination with the at least one profile element of the ischium, ensures good transfer of forces into the implant. Where only part of the ischium is missing or damaged, the attachment section of this embodiment allows the healthy part of the ischium to be preserved.

In a further particularly preferred embodiment, at least one attachment section comprises, at least in sections, an osseointegrative bone contact surface, in particular a trabecular structure, and/or and osseoinductive bone contact surface.

This embodiment allows the implant to be anchored to the patient's skeleton in a particularly reliable manner by the ingrowth of bone tissue.

Here an osseointegrative bone contact surface provides the bone tissue with a structure and/or surface, into which it can grow or to which it can bond. An example of such a bone contact surface is the surface of a titanium alloy and/or a surface of an attachment section approximated to the native trabecular structure of the bone tissue.

If an attachment section is osseoinductive, it not only provides the adjacent bone tissue passively with a biocompatible surface to grow into or onto but actively encourages the growth of bone tissue by means of corresponding chemical compounds or cytokines.

In a further embodiment of the implant of the present invention the joint section comprises an approximately hemispherical recess, into which a universal socket with an articular surface can be inserted or which forms an articular surface.

Such an embodiment of the joint section is able to directly or indirectly receive the femoral head of a hip endoprosthesis. Where it receives the head directly, the hemispherical recess simultaneously forms an articular surface. However, the femoral head is preferably received indirectly, in that an articular cavity with a joint insert or even a joint insert only is inserted into the hemispherical recess. It is therefore possible to execute this in a modular way, i.e. one and the same joint section can receive a plurality of different cavities or inserts, so that the sliding surface can be adapted to the hip replacement being used for the patient. Moreover, this means that possible deformations related to welding the joint section to the profile elements and the at least one plate element are not so critical, since the narrow tolerances required for the articular surface can be observed by the joint insert.

The substantially hemispherical recess preferably approximately simulates the external contour of the joint section. In other words, the joint section preferably has an approximately constant wall-thickness, which is particularly advantageous for welding of the individual components of the implant according to the invention. Even more preferably, the wall-thickness of the joint section is selected taking account of the diameter or thickness of the profile elements and/or the thickness of the at least one plate element.

In a particularly preferred embodiment of the present invention, at least one of the profile elements and preferably all profile elements is/are free from sharp edges.

Such a configuration of the outside of the profile elements and/or its cross-section ensures that the surrounding soft tissue is protected from damage after implantation.

In other words, in this embodiment at least one of the profile elements has a continuously rounded or continuously differentiable cross-section. Consequently, there are no flat surfaces on the circumference of such profile elements that meet each other at an angle, thereby having the potential to create a sharp edge that could damage tissue. Clearly, it is possible in this embodiment for two flat surfaces of the circumference of a profile element to abut each other at an angle as long as the joint is suitably rounded, that is to say a smooth transition is created between the surfaces. The same applies for the end faces of a profile element, if it impinges on the end face of another profile element or is connected to the same.

In a further embodiment of the present invention, the at least one profile element of the frame structure is a hollow profile, at least in sections.

By configuring the at least one profile element as a hollow profile, it is possible to determine the wall-thickness of the profile element in consideration of the wall-thickness of the joint section, the plate element and/or the attachment section and preferably align it. This serves to avoid stress peaks. Moreover, particularly where the profile elements are connected by welding to each other and/or to other components of the implant, this has the advantage that it is possible to achieve a very strong welded joint. Consequently, it is preferable for a profile element to be configured as a hollow profile, at least in the region of a welded joint.

A further advantage of a hollow profile is the associated weight reduction. Here it is preferred that a profile element executed as a continuous hollow profile is used and even more preferably a frame structure, continuously executed as a hollow profile.

It is also advantageous to design the at least one cavity of the frame structure so that it is hermetically sealed, in order to prevent inflammation in this area, for example. This also serves to prevent the creation of potentially sharp edges, which could otherwise result from the entrance to the hollow profile.

In a further preferred embodiment of the present invention, at least one attachment section is provided with at least one connecting element, in particular a through hole, for a fastening element.

In this embodiment of the invention, a stable connection between implant and the patient's bone tissue is achieved at the time of the operation. This has the particular advantage that the patient is soon mobile again, which promotes the healing process and is advantageous for the musculature and ligament apparatus.

If the respective attachment section further comprises an osseointegrative and/or osseoinductive part, this stable connection also provides the necessary primary stability for reliable bone ingrowth.

The connecting element is preferably a through hole formed through an attachment section for receiving a fastening element. For example, screws, clamps or wires can be used as a fastening element.

In a further particularly preferred embodiment, at least one plate element abuts an attachment section and/or a joint section, at least in sections.

This ensures that a plate element is largely and preferably continuously surrounded on its circumference by a profile element, attachment section and/or joint section, thereby protecting tissue adjoining the implant from any damage.

In a particularly preferred embodiment of the implant, substantially two curved profile elements are provided for transferring the joint forces from the joint section, said profile elements being connected on a first side to an attachment element and on the opposite second side to the joint section, wherein the first and second side of each of the profile elements preferably point in opposite directions.

The curvature of the profile element firstly serves to provide a more accurate reconstruction of the pelvic structure and secondly to cushion the induction of joint forces compared with straight profiles.

When it is stated that the first side and the second side of a profile element point in opposite directions, this means that the longitudinal axis of the profile emerging from the end faces of the profile element and/or the vectors lying thereon and pointing away from the profile element are at an angle to each other. Due to the curvature of the respective profile element this is therefore less than 180° on one side but should not be less than 90° and preferably 135°.

In addition, the present invention provides a method for manufacturing a patient-specific implant suitable for reconstructing a joint and at least a part of an adjacent bone structure. To this end, the method includes the following steps. The implant is designed with at least one attachment section for attaching the implant to bone tissue, a frame structure embodied by at least one profile element, at least one plate element, which is surrounded by the frame structure, at least in sections, and at least one joint section, which forms at least part of an artificial joint. Shape data are prepared for an implant designed in this way, forming the basis for subsequent manufacture of the implant.

The structural combination of the at least one plate element and the at least one profile element of the frame structure is a patient-specific solution for replacing a bone structure, which is both quick and cheap to make. If required, the shape of the attachment sections can be adapted to fit the bone tissue to which they are anchored.

The individual elements and sections thus provide a construction kit of structural elements, with which to reconstruct the missing bone tissue in a simple way. The elements and attachment sections can then be made either directly as one body or prefabricated and subsequently joined together.

In a particularly preferred embodiment of the present invention, at least one profile element and/or plate element is bent three-dimensionally.

This means that the manufacturing method can be used to adapt the implant being produced particularly accurately to the anatomy of a patient. In other words, by means of three-dimensional bending it is possible to functionally and cheaply simulate and/or adjust to any arbitrary external contour of a part of the pelvic structure being reconstructed. This provides optimum support for the internal organs in the pelvic floor area and functionally-oriented transmission of forces, such as joint forces, for example. In particular, three-dimensional bending allows a cushioned transfer of forces into the skeleton, since the profile element is located between the joint section and an attachment section.

Three-dimensional or spatial bending is understood to mean the creation of a curvature that does not lie in a single plane, but requires three spatial directions to describe it.

In a particularly preferred embodiment of the present invention, the frame structure, the joint section and/or the at least one plate element is/are connected by means of a welded joint.

The fact that the profile elements of the frame structure, the joint section and/or the at least one plate element are firmly connected to each other and/or with each other by means of a welded joint, serves to provide continuous tissue-friendly support of the internal organs, since, in contrast to the fastening elements, the welded joints do not have any protrusions, such as screw-heads, for example.

Moreover, welded joints are an inseparable connection, ensuring that the implants are durable. Welded joints also represent a highly adaptable joining technique, which allows the implant to be produced cheaply.

In a further particularly preferred embodiment of the present invention, the implant is produced using an additive manufacturing process.

The primary advantage of using an additive manufacturing process is that it is relatively cheap and also allows a complex, patient-specific implant geometry to be produced for relatively little effort. In particular, the use of such a manufacturing process makes it particularly easy to produce the above-mentioned, hermetically sealed hollow cavities that might be present in the implant. An implant manufactured by such a process is preferably made in one piece.

In a further embodiment of the present invention, at least one plate element, the joint section and/or the frame structure are surface-treated, at least in sections.

In the context of the present invention, surface treatment is understood to mean a specific configuration of the surface of the implant material and/or a coating of the same. In this way, it is possible to achieve an osseointegrative or osseoinductive quality of an attachment section, for example. In a similar way, it is possible to ensure that connective tissue adheres to the implant, thereby providing even better support for the internal organs. Furthermore, surface treatment can serve to prevent allergic reactions to the implant material.

BRIEF DESCRIPTION OF THE DRAWINGS

In the accompanying drawings, which are referred to in the detailed description of currently preferred embodiments, elements that have the same function and/or design are designated by the same reference numerals. In the drawings.

DETAILED DESCRIPTION OF PREFERRED EMBODIMENTS

Figure 1:
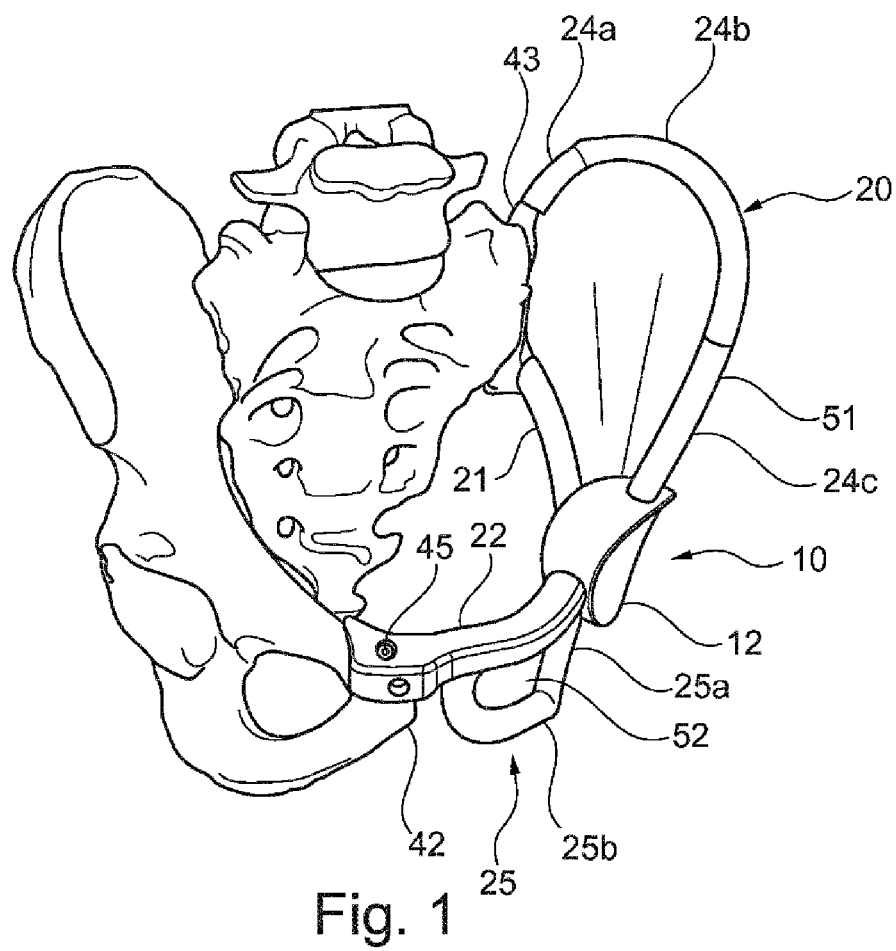
FIG. 1 shows an oblique front view of an implant according to the invention integrated in a pelvic structure to replace part of a pelvic structure.
Figure 2:
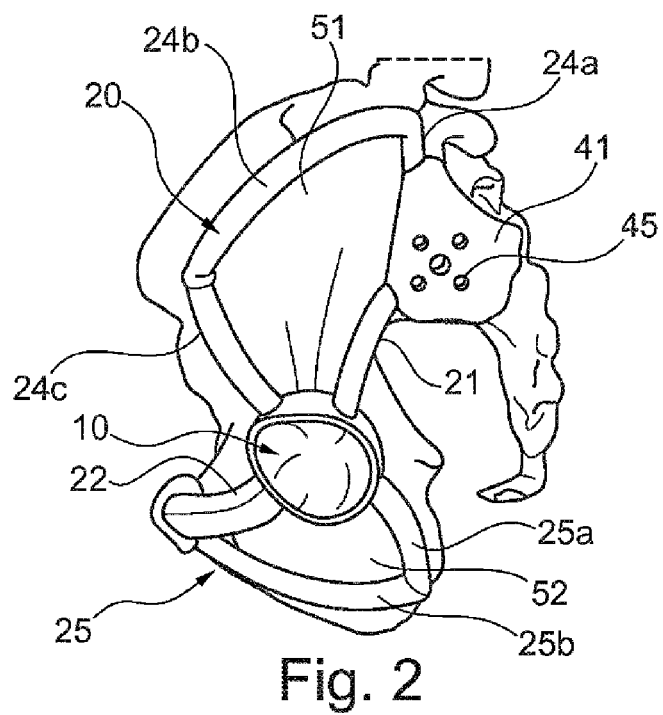
FIG. 2 shows a side view of a pelvic structure according to the invention from FIG. 1 seen from a patient's left side.
Figure 3:
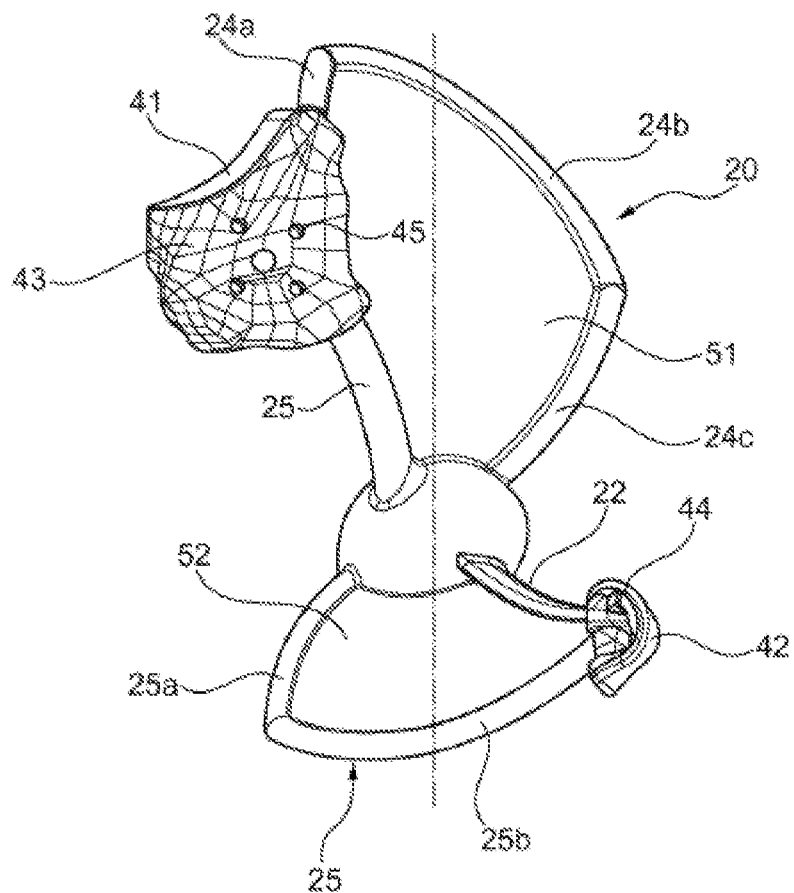
FIG. 3 shows a medial side view of a pelvic structure according to the invention.
Figure 4:
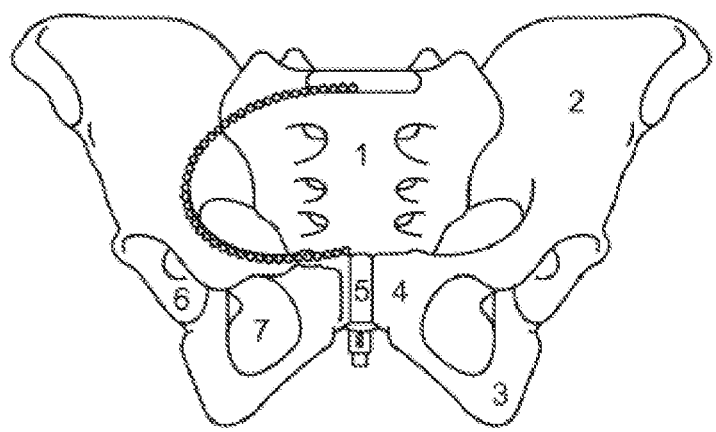
FIG. 4 shows a representative native pelvic structure from the front.

FIG. 1 shows an implant according to the invention for a partial replacement of a pelvic structure including the acetabulum in the implanted state. More precisely, the exemplary embodiment of the implant shown in FIGS. 1 to 3 is replacing the ilium 2, the ischium 3, the pubis 4, the pubis symphysis 5 and, in particular, the acetabulum 6 (see FIG. 4). At one point the implant is connected to the patient's sacrum 1 by means of an attachment section 41 provided on the replacement ilium 2. However, depending upon the extent of the damaged or missing bone tissue, attachment of the attachment section 41 can also take place at a location on the ilium.

The implant in FIG. 1 is further connected at a second point by means of a further attachment section 42 to the pubis 4 of the opposite side of the pelvic structure to that being replaced. Equally, it is possible to attach the attachment section 42 for the pubis to the part of the pubis located on the side of the acetabulum being replaced. This retains the pubis symphysis and allows pliable and cushioned absorption of loads and vibrations in particular.

Depending upon the extent of tissue to be replaced, it can also be expedient to connect the attachment section 42 not to the pubis but instead to the ilium 2 or sacrum 1 on the opposite side of the pelvis to that being replaced. In such a case, both acetabula 6 are replaced accordingly.

As can be seen in FIG. 1, the acetabulum 6 or hip socket has been replaced by a joint section 10. This comprises an approximately hemispherical recess 12, which, as described above, is intended to receive a femoral head. In the illustrated case, the joint section 10 also comprises an approximately hemispherical shape on the opposite or outer side, so that the wall-thickness of the joint section 10 is more or less constant.

Connection of the joint section 10 to the attachment section 41 of the ilium replacement is achieved by means of the profile element 21 and connection of the joint section 10 to the attachment section 42, which, in the illustrated case, is connected to the patient's right pubic bone, is achieved by means of the profile element 22.

As illustrated in FIG. 1, the attachment section 42 comprises a connecting element 45, which, in the present exemplary embodiment, is configured as a through hole. The two through holes 45 provided in the illustrated attachment section 42 serve for fastening the implant by means of fastening elements, such as bone screws, pins, clamps or wires, for example. At least two connecting elements are generally preferred—on the one hand to achieve a solid attachment and, on the other, to have an option during the operation for optimum fastening of the implant to bone tissue, should this be necessary. This ensures that a stable attachment of the implant to the patient's skeleton can be achieved at the time of the operation.

On the other side of the joint section, the attachment section 41 likewise comprises connecting elements 45 in the form of through holes (FIG. 2), with which a firm connection of the implant to the patient's sacrum is achieved during the surgical procedure (primary stability).

As can be seen in FIG. 3, the attachment section of the implant for the ilium 41 and/or the attachment section 42 for the pubis can comprise a surface 43 and/or 44 adapted to the respective bone geometry. The faces of the attachment sections 41 and 42 in contact with the bone tissue are preferably designed to be osseointegrative and/or osseoinductive. If this is the case, the implant is possibly also fastened to the connecting elements 45 by deposition or ingrowth of bone tissue, thereby achieving so-called secondary stability. This also applies to the case where the face of the attachment section 41 and/or 42 facing the bone tissue is not adapted to the surface of the adjacent bone tissue in a patient-specific manner but instead the surface of the patient's bone tissue is adapted to the relevant attachment section during a surgical procedure.

Diverging from the illustrated embodiment, at least one attachment section can also be provided to achieve an attachment to the bone tissue merely by bracing.

In addition to the profile elements 21 and 22, the implant shown in FIGS. 1 to 3 also comprises further profile elements 24a, 24b, 24c for ilium replacement, which, as described above, are preferably connected by means of welded joints.

It is also possible to replace some or all of these profile elements 24a, 24b, 24c by a single profile element, which is appropriately bent or deformed. As can be seen in FIGS. 1 and 2 in particular, the profile elements 24a, 24b, 24c are rounded at their connection points, so as to prevent any damage to surrounding tissue in their implanted state. Profile elements 24a, 24b, 24c substantially form the cranial external contour of the native ilium.

The ilium replacement further comprises a plate element 51, which is particularly intended to support the internal organs. In order to protect the patient's tissue from the circumferential edge of the plate element 51, said plate element is completely enclosed by the frame structure 20, which is embodied by profile elements 21, 24a, 24b, 24c, and also is enclosed by the joint section 10 and the attachment section 41.

Accordingly, the at least one profile element of the frame structure has a cross-section which is larger or thicker, at least in the dimension perpendicular to the plate element. Preferably, the thickness of a profile element along the at least one plate element is at least double, preferably at least five times and most preferably at least ten times the thickness of this plate element.

As can be seen from FIG. 2 in particular, the attachment section 41 is similarly configured as a plate element. However, with such a plate-like attachment section it is not necessary to surround it with profile elements as well, since the edges of the attachment section 41 are not free-standing edges. In other words, the edges of the attachment section 41 fit closely against the bone tissue, thereby preventing any danger to the internal organs. The edges of the attachment section 41 are preferably rounded.

In the implant illustrated in FIGS. 1 to 3, complete replacement 25 of the native ischium 3 is also envisaged. Here the ischium replacement 25 comprises the two profile elements 25a, 25b and a further plate element 52. By means of this extension, the exemplary embodiment of the implant comprehensively maintains the supporting function performed by the native pelvic structure (cf. FIG. 4), which is a considerable advantage.

Diverging from the illustrated embodiment of the implant, the plate element 52 can also be omitted or reconfigured for replacing the ischium 3, in particular in order to allow structures located in this region in the native pelvic structure to be led through or secured.

If the part of the native ischium 3 and pubis 4 replaced by the profile element 25b is to be retained (cf. FIG. 4), the part of the implant intended to replace the ischium can be provided with an additional attachment section (not illustrated).

If this type of bone replacement is necessary or in order to achieve an attachment to the bone tissue that is as stable as possible, it can be advantageous to replace the entire ischium and pubis of one side of the pelvic structure, as shown in FIG. 1.

It should also be noted that, as described above, the pelvic implant according to the invention is not only able to functionally replace the native pelvic structure or a part thereof but, in addition, is cheap to produce, especially by means of additive and/or adaptive manufacturing. After computer-assisted planning of a patient-specific implant according to the invention, subsequent manufacture can be almost completely automated. In this way it is possible to provide the implant quickly, cheaply and customized to the patient.

Depending upon the manufacturing technique used for the implant, the plate elements, profile elements and/or attachment sections can be at least partially preformed prior to assembly of the implant, thereby facilitating assembly of the individual components, particularly if welding is used.

However, it is particularly preferred to use an additive technique to manufacture the implant.

Electron Beam Melting (EBM) and Selective Laser Melting (SLM) are particularly suitable for this. In both methods, a metal powder for processing is applied to a base plate in a thin layer. The powdered material is then locally melted or irradiated by an electron beam or laser beam, forming a solid layer of material once it solidifies. The base plate is then lowered by one layer thickness and powder is reapplied. This cycle is repeated until all layers have been remelted.

It is also possible to use an additive process to produce a mould, which is then used to cast the implant. Similarly, the implant can be produced as a green body using an additive process and then sintered. The use of an additive process is especially advantageous in the context of the pelvic replacement, since the design freedom it offers in creating the structure means that stresses can be equally distributed and material load can be kept to a minimum. It is consequently possible to reduce the material strength. This is particularly true in the case of the EBM and SLM techniques, since neither method requires the removal of casting cores, there is no need to consider material creep behaviour in designing the replacements and, moreover, it is possible to create sealed cavities, for example. Moreover, these techniques produce the end product straightaway instead of an intermediate product, from which the end product then has to be made.

Furthermore, as already described above, the surface of the at least one plate element, the frame structure and/or the joint section can be specially treated, at least in sections, in order to facilitate connection of the surrounding soft tissue or connective tissue with the implant and thereby further improve the supporting function, particularly of the ilium replacement.

Where there is a plate element 52 in the region of the ischium replacement, it can be advantageous if this only fills in the border formed by the profile elements 25a, 25b, 22 and the joint section 10 in sections, in order to facilitate the attachment of musculature, tendons and/or ligaments.

The invention claimed is:

1. An implant for reconstructing an acetabulum and at least part of a pelvic structure of a patient, said implant comprising:
   a frame structure embodied by at least one first hollow profile element for transferring joint forces, wherein the at least one hollow profile element is elongated and has a first end face and a second end face,
   a joint section, which forms at least part of an artificial acetabulum, at least two attachment sections for attaching the implant to bone tissue, wherein a first attachment section is provided for attachment to a sacrum or ilium and a second attachment section is provided for attachment to a pubis, and
   at least one plate element for supporting internal organs, wherein a circumferential edge of the at least one plate element is surrounded by the frame structure at least in sections, wherein the at least one plate element and the at least one hollow profile element of the frame structure are formed as one body, and the at least one plate element and the frame structure are designed for replacing at least part of the pelvic structure,
   wherein the attachment section is located along the circumferential edge,
   wherein the first end face of the at least one hollow profile element is fixed to said joint section and the second end face of the at least one hollow profile element is fixed to one of the attachment sections or to another profile element of the frame structure, and
   wherein the first and second end faces of the at least one profile element point in oppositedirections.

2. The implant according to claim 1, further comprising:
   a second frame structure embodied by at least one profile element to replace at least partof an ischium.

3. The implant according to claim 2,
   wherein the second frame structure further comprises a plate element and/or an attachment section.

4. The implant according to claim 1,
   wherein at least one attachment section of the at least two attachment sections comprises, at least in sections:
   an osseointegrative bone contact surface; and/or
   an osseoinductive bone contact surface.

5. The implant according to claim 1,
   wherein the joint section comprises an approximately hemispherical recess, into which auniversal socket with an articular surface can be inserted or which forms an articular surface.

6. The implant according to claim 1,
   wherein the at least one profile element is free from sharp edges.

7. The implant according to claim 1,
   wherein at least one attachment section of the at least two attachment sections is providedwith at least one connecting element for a fastening element.

8. The implant according to claim 1,
   wherein the at least one plate element abuts an attachment section and/or joint section, atleast in sections.

9. The implant according to claim 1,
   wherein two substantially curved profile elements are provided for transferring the jointforces from the joint section,
   wherein the profile elements are each connected at one end to an attachment element and, at a second end opposite the one end, to the joint section, wherein the first and second end of each of the profile elements point in opposite directions.

10. The implant according to claim 4, wherein the osseointegrative bone contact surface comprises a trabecular structure.

11. The implant according to claim 1, wherein all profile elements are free from sharp edges.

12. The implant according to claim 7, wherein the at least one connecting element comprises a through hole.

\* \* \* \* \*